United States Patent [19]

Genese

[11] 4,237,879
[45] Dec. 9, 1980

[54] EQUIPMENT SETS FOR THE SEQUENTIAL ADMINISTRATION OF MEDICAL LIQUIDS AT DUAL FLOW RATES EMPLOYING PARALLEL SECONDARY LIQUID TUBING AND A 3-WAY VALVE

[75] Inventor: Joseph N. Genese, Waukegan, Ill.

[73] Assignee: Abbott Laboratories, North Chicago, Ill.

[21] Appl. No.: 16,226

[22] Filed: Feb. 28, 1979

[51] Int. Cl.³ .............................................. A61M 5/14
[52] U.S. Cl. ................................................ 128/214 G
[58] Field of Search ........... 128/214 R, 214 C, 214 G, 128/214.2, 227, 274; 222/129.2, 145; 137/112–114

[56] References Cited

U.S. PATENT DOCUMENTS

| | | | |
|---|---|---|---|
| 3,886,937 | 6/1975 | Bobo et al. | 128/214 G |
| 3,965,895 | 6/1976 | Dabney | 128/214 C |
| 4,005,710 | 2/1977 | Zeddies et al. | 128/214 G |
| 4,105,029 | 8/1978 | Virag | 128/214 G |
| 4,116,646 | 9/1978 | Edwards | 55/159 |

*Primary Examiner*—Dalton L. Truluck
*Attorney, Agent, or Firm*—Robert L. Niblack; Aaron L. Hardt; Robert S. Beiser

[57] ABSTRACT

Equipment sets for the sequential administration of medical liquids wherein a primary liquid can be administered at a flow rate independent of the flow rate of a secondary liquid, and including a barrier substantially impervious to air to prevent the inadvertent administration of air when the secondary liquid is depleted. The sets of this invention provide parallel flow paths for the secondary liquid to insure that the flow of primary liquid is interrupted while the secondary liquid is flowing. A 3-way valve is provided in the first parallel branch to facilitate priming of the set.

16 Claims, 4 Drawing Figures

EQUIPMENT SETS FOR THE SEQUENTIAL ADMINISTRATION OF MEDICAL LIQUIDS AT DUAL FLOW RATES EMPLOYING PARALLEL SECONDARY LIQUID TUBING AND A 3-WAY VALVE

BACKGROUND OF THE INVENTION

The present invention relates to equipment sets for the administration of medical liquids to a patient, and more particularly, to systems and equipment sets for the sequential administration of a plurality of medical liquids employing parallel flow of the secondary liquid to insure that the flow of the primary liquid is interrupted while the secondary liquid is flowing.

The parenteral administration of medical liquids to patients is a long established practice. Liquids including amino acids, blood, dextrose, electrolytes, and saline are commonly administered to patients over prolonged periods of time. Generally, these liquids are administered from a glass bottle or plastic bag suspended above the patient and containing 250-2,000 ml. of the liquid. Such prolonged infusions commonly are administered at a flow rate of 10-150 ml./hr.

Frequently, the patient must receive an additive or secondary liquid while the prolonged infusion is being administered. Preferably, this secondary liquid should be administered through the same hypodermic needle to avoid unnecessary pain and trauma to the patient of additional venipunctures. To avoid dilution and incompatability problems, it is also preferable that the flow of the primary liquid employed in the prolonged infusion be temporarily interrupted, the secondary liquid administered and the flow of the primary liquid resumed. Generally, the secondary liquid will be administered at a flow rate of 50-250 ml./hr.

Abbott Laboratories, North Chicago, Ill. manufactures a y-type set for the sequential administration of primary and secondary liquids. These VENOSET piggyback sets allow the prolonged infusion of a primary liquid to be temporarily halted by means of a backcheck valve in the primary liquid flow path to administer a secondary liquid without the need for a new venipuncture. Then, when the secondary liquid has been depleted, the backcheck valve automatically opens to resume flow of the primary liquid. An important characteristic of this system is that the secondary liquid container must be suspended at a higher height than the primary liquid container to establish the liquid pressure differential that closes the backcheck valve in the primary liquid flow path.

A similar system is disclosed in U.S. Pat. No. 3,886,937 granted June 3, 1975 to D. Bobo, et al., assigned to American Hospital Supply Corp., and entitled "Medical Administration Set for Dispensing Plural Medical Liquids." Another similar system is disclosed in U.S. Pat. No. 4,105,029 granted Aug. 8, 1978 to R. Virag, assigned to Baxter Travenol and entitled "Intravenous Solution Set Having An Air Access Site and Constricted Inner Diameter Portion."

An inherent disadvantage of the above-mentioned prior art medical liquid administration systems is that they each resume the flow of primary liquid at the rate the secondary liquid had been flowing. Because the preferred flow rate of the secondary liquid is generally greater than the preferred flow rate of the primary liquid, when the primary liquid resumes flow at that rate, the patient can be administered an excessive amount of primary liquid, unless the flow rate of the primary liquid is adjusted to the preferred primary liquid flow rate soon after the flow of primary liquid resumes.

A remedy to the above-described disadvantage would appear to be provided by simply incorporating flow control devices into both the primary and secondary liquid flow paths. However, while this remedy does provide dual flow rates for the primary and secondary liquids, it is unacceptable. That is, because the common tube of the y-set must be able to accommodate both flow rates, when the primary liquid is flowing at a slower rate than the secondary liquid was, there will be an unfilled volume or void in the common tube. To fill that void, air will be drawn into the common tube from the depleted secondary container. That air will then be driven into the patient by the weight of the primary liquid, thereby causing a serious embolism and perhaps, the patient's death.

Accordingly, it will be apparent that an efficacious system for the sequential administration of medical liquids at dual flow rates would be advantageous to the medical profession.

SUMMARY OF THE INVENTION

The primary object of the present invention therefore, is to provide equipment sets for the sequential administration of medical liquids at dual flow rates that will not draw air from the secondary container when the secondary liquid has been depleted.

In accordance with this and other objects, there is provided by the present invention an equipment set for the sequential administration of medical liquids to a patient including a primary tube, a secondary tube, and a common tube all connected in fluid communciation to form a primary liquid flow path and a secondary liquid flow path. The primary liquid flow path includes the primary and common tubes, while the secondary liquid flow path includes the secondary and common tubes.

The primary tube includes a primary valve which allows primary liquid to flow from the primary container whenever the height of primary liquid is greater than or equal to the height of the secondary liquid in the system. The primary valve, which can be a backcheck valve, prevents primary liquid from flowing out of the primary container whenever the height of the primary liquid is less than the height of the secondary liquid in the system.

The secondary tube has two parallel branches. They are both connected to the common tube; the first near its distal end and the second proximal to the distal end. The first has a one-way valve to prevent the reverse flow of primary liquid therethrough and a 3-way valve to facilitate priming of the entire secondary tube. Thus, the secondary liquid flow path comprises a first flow path defined by portions of the secondary tube common to both branches, the first branch and the common tube and a second flow path defined by portions of the secondary tube common to both branches, the second branch and the common tube.

To establish the dual flow rates of the primary and secondary liquids, a second flow control means in the second flow path for adjusting the flow rate of the secondary liquid and a first flow control means on the common tube between the first and second branches of the secondary tube for adjusting the flow rate of the primary and secondary liquid passing therethrough are provided. Thus, secondary liquid flows through the secondary liquid flow path at a rate controlled by the first and second control means, while primary liquid flows through the primary liquid flow path at a rate independent of the flow rate of the secondary liquid. An air barrier in the second liquid flow path that is substantially impervious to air is provided to insure that no air is drawn from the secondary container when the secondary liquid is depleted.

BRIEF DESCRIPTION OF THE DRAWING

Other objects and attendant advantages will become obvious to those skilled in the art by reading the following detailed description in connection with the accompanying drawing, wherein like reference characters designate like or corresponding parts throughout the several figures thereof and wherein.

DETAILED DESCRIPTION OF THE INVENTION

Figure 1:
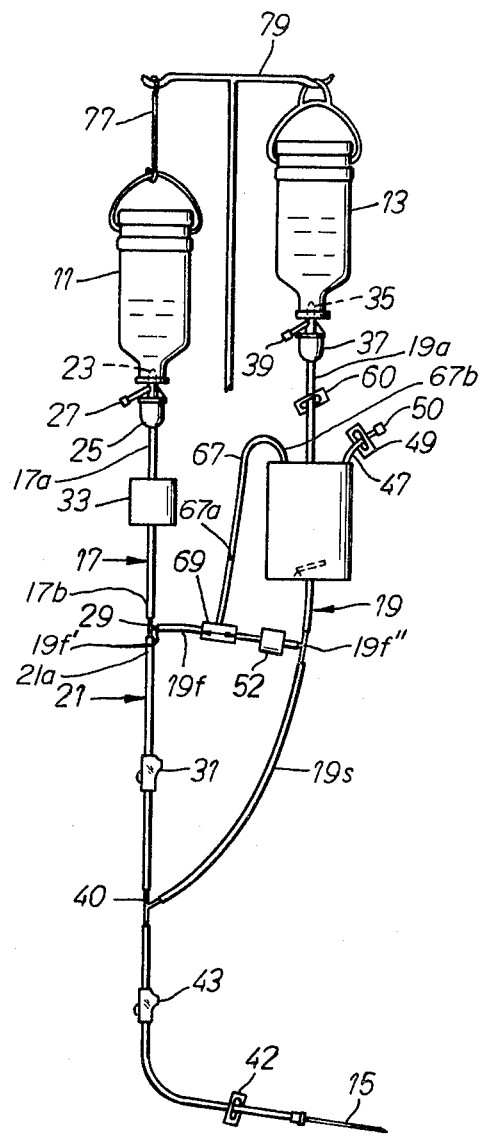
FIG. 1 is a front elevational view of one embodiment of the efficacious equipment sets for the sequential administration of medical liquids at dual flow rates contemplated by this invention.

Referring to the drawing, there is shown in FIG. 1, a diagram of the basic elements of the equipment sets for the sequential administration of medical liquids at dual flow rates contemplated by this invention.

FIG. 1 depicts a primary liquid container 11 that contains a primary medical liquid to be administered to a patient for a prolonged period of time. FIG. 1 also depicts a secondary liquid container 13 that contains a secondary medical liquid to be administered to the patient for a relatively short period of time, during which time the administration of the primary liquid will be temporarily interrupted. Containers 11 and 13 can be glass bottles, plastic flexible bags, or any other suitable container.

Primary container 11 and secondary container 13 are connected in fluid communication to a conventional hypodermic needle 15 through a primary tube 17, a secondary tube 19, having a first branch 19f and a second branch 19s, and a common tube 21. Thus, the primary liquid flow path from primary container 11 to needle 15 comprises primary tube 17 and common tube 21. Likewise, the secondary liquid flow path from secondary container 13 to needle 15 comprises all of secondary tube 19 and common tube 21. The secondary liquid flow path comprises a first flow path defined by the portions of the secondary tube common to both branches, the first branch and the common tube and a second flow path defined by portions of the secondary tube common to both branches, the second branch and the common tube.

The distal end 17a of primary tube 17 is in fluid communication with primary container 11, preferably by means of a piercing pin 23 inserted into a puncturable closure of container 11. Piercing pin 23 can have an integral drip chamber 25, and when container 11 is a glass bottle, as shown in the set of FIG. 1, an integral, filtered air vent 27. Such piercing pins, drip chambers and air vents are well known in the medical practice and need not be more fully explained here.

The proximal end of primary tube 17 is joined in fluid communication to the distal end of common tube 21, preferably by a y-tube 29, it being understood that the primary, secondary and common legs of y-tube 29 constitute a portion of the primary, secondary and common tubes 17, 19 and 21, respectively.

Primary tube 17 includes a primary valve 33 that allows primary liquid to flow from primary container 11 whenever the height of the primary liquid is greater than or equal to the height of the secondary liquid in the set of FIG. 1. Further, primary valve 33 prevents the flow of primary liquid from primary container 11 whenever the height of the primary liquid is less than the height of the secondary liquid in the set.

While primary valve 33 has been shown in FIG. 1 as being spaced from the proximal end of primary tube 17, it will be readily apparent that primary valve 33 can be incorporated into the primary leg of y-tube 29, if so desired. For example, primary valve 33 can be a conventional, one-way, backcheck valve mounted within the primary leg of y-tube 29.

The distal end 19a of secondary tube 19 is in fluid communication with secondary container 13, preferably, by means of a piercing pin 35 inserted into a puncturable closure of container 13. Piercing pin 35 can have an integral drip chamber 37, and when container 13 is a glass bottle, as shown in FIG. 1, an integral, filtered air vent 39. Secondary tube 19 has first and second parallel branches 19f, 19s connected in fluid communication to common tube 21. First branch 19f is joined to the distal end 21a of common tube 21, preferably by a y-tube 29 and second branch 19s is joined to common tube 21 on the proximal side of the connection to first branch 19f, preferably, by a y-tube 40.

Common tube 21 has a first flow control 31 between its connections to first branch 19f and second branch 19s for independently adjusting the rate of flow of the primary and secondary liquid passing therethrough. Second flow control 43 is located in the second flow path and controls the flow rate of secondary liquid therethrough. Preferably, as shown in FIG. 1, first and second flow controls 31, 43 can be roller clamps. However, they can be any other adjustable device that can reliably maintain a desired liquid flow rate. As shown in FIG. 1, common tube 21, preferably, has a slide clamp 42 at its proximal end.

As shown in FIG. 1, an air barrier 44 is located in secondary tube 19, which is its preferred location. However, air barrier 44 can be located in the common tube portion of the second flow path if so desired. Likewise, for increased reliability of the system, a plurality of air barriers 44 can be located in either the secondary tube 19, common tube 21, or both. Futher, while air barrier 44 is shown spaced from the proximal end of secondary tube 19, it will be readily apparent that air barrier 44 can be incorporated into the secondary or common tube leg of y-tube 40.

Figure 4:
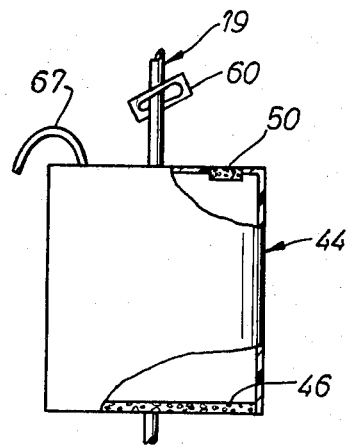
FIG. 4 is a front elevational view, partially in cross-section, of a portion of the set of FIG. 1 depicting an alternate embodiment of the air barrier thereof.

As shown in the set of FIG. 1, air barrier 44 comprises a housing having an inlet and outlet in fluid communication with secondary tube 19 and constitutes a portion of it. The outlet from the housing is covered by a float valve 45 which floats away from the outlet when liquid is present, but seats or closes over the outlet when liquid is not present. Alternatively, the outlet can be covered by membrane filter 46 which is impermeable to air when wet, as shown in FIG. 4. The hydrophilic filter can be formed from materials such as a cellulose acetate material produced by the Millipore Filter Corporation of Bedford, Mass. or the Sartorius-Membranfilter GmbH of Weender Landstr, West Germany.

As shown in FIG. 1, the housing of air barrier 44 can have an associated air vent tube 47 having a slide clamp 49 and a filtered opening 50. Air vent 47 allows air to be vented from the secondary tube when it is being primed, or back-primed, and by manual control, permits secondary tube 19 to be drained of any secondary liquid remaining therein when air reaches air barrier 44.

Alternatively, opening 50 can be filtered by a hydrophobic membrane filter which is permeable by air, but not liquids, as shown in FIG. 4. The hydrophobic filters can be formed of polyfluorotetraethylene, hexafluoropropylene/tetrafluoroethylene copolymer, or other suitable materials. One such filter is made of Gelman ANH-450 material made by Gelman Instruments of Ann Arbor Mich. When such a hydrophobic filter is used, slide clamp 49 can be eliminated.

As illustrated in FIG. 1, first branch 19f has a one-way valve 52 that permits liquid to flow towards its proximal end 19f' at y-tube 29, but generally prevents the flow of liquid through its proximal end towards its distal end 19f''. Preferably, valve 52 can be a conventional, one-way, backcheck valve.

To enable secondary tube 19 to be back-primed with primary liquid, the set is provided a priming tube 67 and a 3-way valve 69. Preferably, 3-way valve 69 can be a 3-way stopcock. 3-way valve 69 is located in the first branch 19f of secondary tube 19 on the proximal side 19f' of one-way valve 52. 3-way valve 69 has a housing with three ports for the flow of liquid into and out of the housing and means for alternately connecting only the first and second, second and third, or first and third ports in fluid communication.

Figure 2:
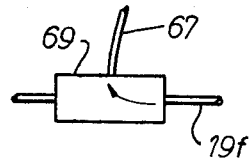
FIGS. 2 and 3 are front elevational views of a portion of the set of FIG. 1 depicting the 3-way valve thereof.
Figure 3:
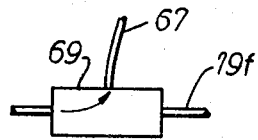

As seen in FIGS. 1—3, the first port of valve 69 is disposed in first branch 19f near its proximal end 19f', the second port is disposed in first branch 19f distally from the first port, and the third port is joined to the proximal end 67a of priming tube 67. The distal end 67b of priming tube 67 is joined to a port of air barrier 44. Alternatively, the distal end 67b of priming tube 67 can be joined to secondary tube 19 at other locations on the distal side 67b of one-way valve 52 suitable for back-priming secondary tube 19.

As shown in FIG. 1, 3-way valve 69 has been adjusted by a means therefor, e.g., a handle, so that the first and second ports are joined in fluid communication. In FIG. 2, the second and third ports are joined and in FIG. 3, the first and third ports are joined.

For simplicity, the equipment sets of this invention have been depicted and described as integral units. It is apparent, however, that the sets can be manufactured and assembled in subsets of the entire set and that each subset will accordingly be provided such resealable closures, piercing means, adapters, etc. as are necessary to permit their easy assemblage into the complete set at an appropriate time. It will also be apparent that the several components of the sets can be interchanged or combined in combinations other than those specifically depicted.

Operation of the System

As depicted in FIG. 1, primary container 11 is suspended in space at a height above the patient by means of a hook 77 and stand 79. It will be apparent that other means for suspending the containers of this invention are well known.

The set depicted in FIG. 1 prevents the flow of primary liquid through first branch 19f when the supply of secondary liquid is depleted from secondary container 13 by means of the one-way valve 52 located in first branch 19f. Otherwise, primary liquid would flow to the patient at exactly the same rate that the secondary liquid had been.

If secondary tube 19 is to be back-primed with primary liquid without priming tube 67, valve 52 would necessitate that back-priming liquid to proceed past first flow control 31 into second branch 19s. After the set has been initially primed and in operation, it is generally preferred to maintain the current setting of first flow control means 31. Thus, back-priming the set solely via second branch 19s would be time consuming, in such instances. Accordingly, the sets of this invention include a priming tube 67 joined to a 3-way valve 69 that can be adjusted to allow primary liquid to flow into secondary tube 19 in circumvention of one-way valve 52 and first flow control means 31. It will be apparent that secondary tube 19 can be primed in other manners than by back-priming, if so desired.

To insure that all the air that might be forced into the patient has been removed from a set, the set is initially primed by first closing all slide clamps 42, 49 and 60, if present. Valve 69 is adjusted so that its first and second ports are connected, as shown in FIG. 1. Piercing pin 23 is then inserted into the resealable closure of primary container 11. First flow control 31 and second flow control 43 are fully opened. Slide clamp 42 is opened to allow primary liquid to flow through the primary liquid flow path and force all the air therefrom that might be forced into the patient. Slide clamp 42 is then closed.

Slide clamps 49 or 60, if present, are then opened. Primary liquid will then flow distally through first branch 19f for a moment, until one-way valve 52 closes. Valve 69 is then adjusted so that its second and third ports are connected, as shown in FIG. 2. Primary liquid will then flow into, or back-prime, secondary flow path 19 via second branch 19s and force all the air from air barrier 44. Slide clamps 49 and 60, if opened, are then closed. During the initial priming of secondary tube 19, it is advantageous to hold secondary tube 19 at a height well below primary container 11. When secondary tube 19 has been primed, it is secured in a convenient place until its subsequent use.

Common tube 21, which preferably has an adapter at its proximal end open to the flow of liquid therefrom, is next connected to needle 15, which will generally have been already inserted into a vein of the patient. Slide clamp 42 will then be opened to allow primary liquid to flow through the primary liquid flow path to the patient's vein. First flow control 31 is then adjusted to a setting that will provide the desired flow rate for a prolonged infusion of primary liquid into the patient, generally 10–150 ml./hr. As is well known in the medical practice, that flow rate can be visually observed by viewing and counting drops passing through the primary drip chamber 25.

Subsequently, when it is desired to administer a secondary liquid to a patient, piercing pin 35 of secondary tube 19 is inserted into the resealable closure of secondary container 13. If any portion of secondary tube 19 has not already been primed, it can now be primed with secondary container 13 held at a height well below primary container 11, secondary tube slide clamps 49 and 60 opened, common tube slide clamp 42 closed and 3-way valve 69 adjusted so that its first and third ports are connected as shown in FIG. 3, to allow primary liquid to flow directly into priming tube 67. Primary liquid then is allowed to flow into, or back-prime, secondary tube 19 via priming tube 67 and second branch 19s until all the air that can be forced into the patient has been expelled from secondary tube 19. 3-way valve 69 is then adjusted so that its first and second ports are connected, as shown in FIG. 1.

Secondary container 13 is then suspended in space from stand 79 at a height substantially greater than the height of primary container 11, thereby immediately causing primary valve 33 to close. Common tube slide clamp 42 is then opened and secondary flow control 43 adjusted to provide a combined parallel flow rate, typically 50–250 ml./hr., for the secondary liquid, which will then flow until the secondary container 13 is depleted. It will be apparent that the initial liquid flowing from secondary tube 19 will be the primary liquid with which it was primed.

When the height of primary liquid in the system of FIG. 1 becomes greater than the height of the secondary liquid, primary valve 33 will immediately open and allow primary liquid to flow from the primary container at the flow rate to which primary flow control 31 is adjusted. The primary flow rate is independent of the secondary flow rate. In those instances where it is less than or equal to the secondary flow rate, both primary and secondary liquid will flow through common tube 21, until air reaches air barrier 44 in the secondary tube and the height of secondary liquid in first branch 19f becomes less than the height of primary liquid in primary container 11. Then only primary liquid will enter common tube 21. Air barrier 44 and one-way valve 52 then prevent air from being drawn into common tube 21 through the second flow path and eventually to the patient's vein.

When primary container 11 becomes depleted of primary liquid, the primary piercing pin 23 is merely removed therefrom and inserted into the resealable closure of a new primary container, which is then suspended in place of the previous container. If primary container 11 had become empty, it will be necessary to reprime the entire system as when the first primary container was administered.

When secondary container 13 becomes depleted of secondary liquid, it can be left empty until another secondary liquid is to be administered. When another secondary liquid is to be administered, the secondary piercing pin 35 is merely removed from secondary container 13 and inserted into a new secondary liquid container. The secondary tube 19 must then be back-primed, as when the first secondary container was administered.

Having described the invention in specific detail and exemplified the manner in which it may be carried into practice, it will now be readily apparent to those skilled in the art that innumerable variations, applications, modifications and extensions of the basic principles involved may be made without departing from its sphere or scope.

I claim:

1. A set for the sequential administration of medical liquids to a patient, said set comprising:
    a primary tube for the flow of a primary liquid therethrough and including a primary valve for controlling the flow of liquid through said primary tube,
    a secondary tube having first and second parallel branches for the parallel flow of a secondary liquid therethrough,
    a common tube having its distal end connected in fluid communication with the proximal ends of said primary tube and said first branch of said secondary tube, the proximal end of said second branch of said second tube connected in fluid communication to said common tube at a location on said common tube proximal to said connection of said first branch to said common tube, said proximal end of said second branch being open for the flow of liquid therefrom to form a primary liquid flow path comprising said primary tube and said common tube and a secondary liquid flow path comprising the combined flow of secondary liquid through a first flow path defined by the portions of said secondary tube common to both branches, said first branch and said common tube and a second flow path defined by the portions of said secondary tube common to both branches, said second branch and said common tube,
    a one-way valve in said first branch of said secondary tube that only allows liquid to flow therethrough towards the proximal end of said first branch,
    a 3-way valve in said first branch of said secondary tube and located on the proximal side of said one-way valve, said 3-way valve comprising a housing with three ports for the flow of liquid into and out of said housing, said first port located on the proximal side of said 3-way valve, said second port on the distal side of said 3-way valve, said third port joined to the proximal end of a priming tube joined at its distal end to said secondary tube in fluid communication with the distal side of said one-way valve, and means for alternately connecting only said first and second ports, said second and third ports, or said first and third ports in fluid communication,
    a first flow control means on said common tube between the distal end thereof and said connection to said second branch of said secondary tube for adjusting the flow rate of said primary and secondary liquid therethrough,
    a second flow control means in said second flow path for adjusting the flow rate of said secondary liquid therethrough, and
    an air barrier in said second flow path substantially impervious to air while said set is in use and preventing the flow of air therethrough,
    whereby said secondary liquid flows through said secondary liquid flow path at a rate controlled by said first and second flow control means and said primary liquid flows through said primary liquid flow path at a rate independent of the flow rate of said secondary liquid.

2. The set defined in claim 1, wherein said 3-way valve is a 3-way stopcock.

3. The set defined in claim 1, wherein said air barrier comprises a hydrophilic membrane disposed in a housing having an inlet and outlet in fluid communication with said second flow path.

4. The set defined in claim 1, wherein said air barrier comprises a mechanical valve disposed in a housing having an inlet and outlet in fluid communication with said second flow path.

5. The set defined in claim 4, wherein said mechanical valve is a float valve.

6. The set defined in claim 1, wherein said air barrier is located between the ends of said second branch of said secondary tube.

7. The set defined in claim 1, wherein said air barrier is located between the ends of said common tube.

8. The set defined in claim 3 or 4, wherein said housing includes an air vent.

9. The set defined in claim 8, wherein said air vent is covered by a hydrophobic membrane.

10. The set defined in claim 1, wherein said primary tube further includes a primary piercing pin at its distal end for insertion into a container for a primary medical liquid and a drip chamber for forming drops of said primary liquid.

11. The set defined in claim 10, wherein said secondary tube further includes a secondary piercing pin at its distal end for insertion into a container for a secondary medical liquid, and a drip chamber for forming drops of said secondary liquid.

12. The set defined in claim 10 or 11, wherein said piercing pins and drip chambers are integral.

13. The set defined in claim 10 or 11, wherein said piercing pins have integral air vents.

14. The set defined in claim 1, wherein said second flow control means is on said second branch of said secondary tube.

15. The set defined in claim 1, wherein said second flow control means is on said common tube.

16. The set defined in claim 1, wherein said primary valve is further characterized as a one-way valve that allows said primary liquid to flow towards said common tube, but prevents the flow of said secondary liquid into said primary tube.

* * * * *

UNITED STATES PATENT AND TRADEMARK OFFICE
CERTIFICATE OF CORRECTION

PATENT NO. : 4,237,879
DATED : December 9, 1980
INVENTOR(S) : Joseph N. Genese

It is certified that error appears in the above-identified patent and that said Letters Patent are hereby corrected as shown below:

Column 5, line 23, 19f should read 19f'.

Column 5, line 25, 19f should read 19f".

Column 5, line 32, 19f should read 19f'.

Column 5, line 38, 19f, second occurrence, should read 19f'.

Signed and Sealed this

Twenty-first Day of April 1981

[SEAL]

Attest:

RENE D. TEGTMEYER

*Attesting Officer*     *Acting Commissioner of Patents and Trademarks*